(12) United States Patent
Berthon-Jones et al.

(10) Patent No.: US 7,302,950 B2
(45) Date of Patent: Dec. 4, 2007

(54) PATIENT INTERFACE FOR RESPIRATORY APPARATUS

(75) Inventors: Michael Berthon-Jones, Leonay (AU); Michel Calluaud, Hunter's Hill (AU); Christopher Edward Lynch, Turramurra (AU); Colin Edward Sullivan, Birchgrove (AU)

(73) Assignee: ResMed Limited, Bella Vista (AU)

( * ) Notice: Subject to any disclaimer, the term of this patent is extended or adjusted under 35 U.S.C. 154(b) by 470 days.

(21) Appl. No.: 10/385,701

(22) Filed: Mar. 12, 2003

(65) Prior Publication Data

US 2003/0154980 A1 Aug. 21, 2003

Related U.S. Application Data

(60) Division of application No. 08/524,148, filed on Sep. 6, 1995, now abandoned, which is a continuation of application No. 07/994,153, filed on Dec. 21, 1992, now abandoned.

(30) Foreign Application Priority Data

Dec. 20, 1991 (AU) .................................... PL0148

(51) Int. Cl.
*A61M 16/00* (2006.01)
*A62B 18/02* (2006.01)
*F16L 11/00* (2006.01)

(52) U.S. Cl. ........................... 128/204.23; 128/207.13; 138/118

(58) Field of Classification Search ........... 128/200.24, 128/200.28, 201.22, 202.27, 203.12, 203.29, 128/204.11, 204.12, 204.18, 205.25, 205.27, 128/206.12, 206.13, 206.14, 206.21, 206.27, 128/206.28, 207.11, 207.13, 207.18; 138/118, 138/119, 121

See application file for complete search history.

(56) References Cited

U.S. PATENT DOCUMENTS 853,431 A 5/1907 Allen (Continued)

FOREIGN PATENT DOCUMENTS

AU A-62221/90 3/1991

(Continued)

OTHER PUBLICATIONS

Internaitonal Application No. PCT/US90/02800 filed May 21, 1990.

(Continued)

*Primary Examiner*—Justine R. Yu
*Assistant Examiner*—Shumaya Ali
(74) *Attorney, Agent, or Firm*—Nixon & Vanderhye P.C.

(57) ABSTRACT

A patient interface assembly adapted to be connected to a gas supply pump to deliver breathable gas to the inlet of a patient's respiratory system comprises a supply conduit, a patient interface, a branch swivel connector including a Y-piece and an elbow that swivels relative to the Y-piece, the branch swivel connector being adapted to be located to the rear of a patient's head in use and being connected to the supply conduit. A pair of inlet tubes each have a first end positioned in use near a mouth of a patient and are connected to the nose mask, a middle portion arranged to pass across a cheek of a patient and an end portion being joined to the Y-piece of the branch connector. The inlet tubes have a flat configuration and are provided with a plurality of internal ribs which prevent the tubes being crushed. A strap is secured to the patient interface and adapted to pass around the sides and rear of the head to hold the patient interface in position on the head.

19 Claims, 7 Drawing Sheets

U.S. PATENT DOCUMENTS

| | | | |
|---|---|---|---|
| 1,081,745 A | 12/1913 | Johnston et al. | |
| 1,632,449 A * | 6/1927 | McKessson | 128/206.24 |
| 2,931,358 A | 5/1960 | Sheridan | |
| 3,099,985 A | 8/1963 | Wilson et al. | |
| 3,400,714 A | 9/1968 | Sheridan | |
| 3,502,100 A | 3/1970 | Jonson | |
| 3,559,638 A | 2/1971 | Potter | |
| 3,720,235 A * | 3/1973 | Schrock | 138/137 |
| 3,726,270 A | 4/1973 | Griffis et al. | |
| 3,741,208 A | 6/1973 | Jonsson et al. | |
| 3,756,244 A * | 9/1973 | Kinnear et al. | 128/207.14 |
| 3,783,893 A | 1/1974 | Davison | |
| 3,802,431 A | 4/1974 | Farr | |
| 3,859,995 A | 1/1975 | Colston | |
| 3,867,946 A | 2/1975 | Huddy | |
| 3,903,875 A | 9/1975 | Hughes | |
| 3,914,994 A | 10/1975 | Banner | |
| 3,932,054 A | 1/1976 | McKelvey | |
| 3,985,467 A | 10/1976 | Lefferson | |
| 3,992,598 A | 11/1976 | Welsh et al. | |
| 3,995,661 A | 12/1976 | Van Fossen | |
| 4,018,221 A | 4/1977 | Rennie | |
| 4,109,749 A | 8/1978 | Sweet | |
| 4,119,096 A | 10/1978 | Drews | |
| 4,206,754 A | 6/1980 | Cox et al. | |
| 4,249,527 A | 2/1981 | Ko et al. | |
| 4,257,422 A * | 3/1981 | Duncan | 604/266 |
| 4,301,833 A | 11/1981 | Donald, III | |
| 4,312,235 A | 1/1982 | Daigle | |
| 4,387,722 A | 6/1983 | Kearns | |
| 4,396,034 A | 8/1983 | Cherniak | |
| 4,406,283 A | 9/1983 | Bir | |
| 4,448,058 A | 5/1984 | Jaffe et al. | |
| 4,449,525 A | 5/1984 | White et al. | |
| 4,481,944 A | 11/1984 | Bunnell | |
| 4,499,914 A | 2/1985 | Schebler | |
| 4,519,399 A | 5/1985 | Hori | |
| 4,530,334 A | 7/1985 | Pagdin | |
| 4,558,710 A | 12/1985 | Eichler | |
| 4,579,114 A | 4/1986 | Gray et al. | |
| 4,592,880 A | 6/1986 | Murakami | |
| 4,641,647 A | 2/1987 | Behan | |
| 4,644,947 A | 2/1987 | Whitwam et al. | |
| 4,648,398 A | 3/1987 | Agdanowski et al. | |
| 4,655,213 A | 4/1987 | Rapoport et al. | |
| 4,676,241 A | 6/1987 | Webb et al. | |
| 4,677,975 A | 7/1987 | Edgar et al. | |
| 4,686,974 A | 8/1987 | Sato et al. | |
| 4,747,403 A | 5/1988 | Gluck et al. | |
| 4,773,411 A | 9/1988 | Downs | |
| 4,774,946 A | 10/1988 | Ackerman et al. | |
| 4,795,314 A | 1/1989 | Prybella et al. | |
| 4,802,485 A | 2/1989 | Bowers et al. | |
| 4,819,629 A | 4/1989 | Jonson | |
| 4,827,922 A | 5/1989 | Champain et al. | |
| 4,827,964 A | 5/1989 | Guido et al. | |
| 4,838,258 A | 6/1989 | Dryden et al. | |
| 4,856,506 A | 8/1989 | Jinotti | |
| 4,870,960 A | 10/1989 | Hradek | |
| 4,870,963 A | 10/1989 | Carter | |
| 4,878,491 A * | 11/1989 | McGilvray, III | 128/201.11 |
| 4,913,401 A | 4/1990 | Handke | |
| 4,915,105 A | 4/1990 | Lee | |
| 4,928,684 A | 5/1990 | Breitenfelder et al. | |
| 4,938,210 A | 7/1990 | Shene | |
| 4,938,212 A | 7/1990 | Snook et al. | |
| 4,944,310 A | 7/1990 | Sullivan | |
| 4,957,107 A | 9/1990 | Sipin | |
| 4,971,050 A | 11/1990 | Bartos | |
| 4,986,269 A | 1/1991 | Hakkinen | |
| 4,989,599 A | 2/1991 | Carter | |
| 5,005,571 A | 4/1991 | Dietz | |
| 5,009,635 A | 4/1991 | Scarberry | |
| 5,024,219 A | 6/1991 | Dietz | |
| 5,046,491 A | 9/1991 | Derrick | |
| 5,048,515 A | 9/1991 | Sanso | |
| 5,062,420 A * | 11/1991 | Levine | 128/204.18 |
| 5,063,922 A | 11/1991 | Hakkinen | |
| 5,063,938 A | 11/1991 | Beck et al. | |
| 5,065,756 A | 11/1991 | Rapoport | |
| 5,099,837 A | 3/1992 | Russel, Sr. et al. | |
| 5,105,354 A | 4/1992 | Nishimura | |
| 5,107,830 A | 4/1992 | Younes | |
| 5,107,831 A | 4/1992 | Halpern et al. | |
| 5,117,819 A | 6/1992 | Servidio et al. | |
| 5,129,390 A | 7/1992 | Chopin et al. | |
| 5,134,995 A | 8/1992 | Gruenke et al. | |
| 5,137,017 A | 8/1992 | Salter | |
| 5,148,802 A | 9/1992 | Sanders et al. | |
| 5,161,525 A | 11/1992 | Kimm et al. | |
| 5,165,398 A | 11/1992 | Bird | |
| 5,178,138 A | 1/1993 | Walstrom et al. | |
| 5,183,983 A | 2/1993 | Knop | |
| 5,195,528 A | 3/1993 | Hok | |
| 5,199,424 A | 4/1993 | Sullivan et al. | |
| 5,203,343 A | 4/1993 | Axe et al. | |
| 5,230,330 A | 7/1993 | Price | |
| 5,231,979 A | 8/1993 | Rose et al. | |
| 5,231,983 A | 8/1993 | Matson et al. | |
| 5,239,994 A | 8/1993 | Atkins | |
| 5,239,995 A | 8/1993 | Estes et al. | |
| 5,243,971 A | 9/1993 | Sullivan et al. | |
| 5,245,995 A | 9/1993 | Sullivan et al. | |
| 5,259,373 A | 11/1993 | Gruenke et al. | |
| 5,271,391 A | 12/1993 | Graves | |
| 5,280,784 A | 1/1994 | Kohler | |
| 5,293,864 A | 3/1994 | McFadden | |
| 5,303,700 A | 4/1994 | Weismann et al. | |
| 5,305,787 A | 4/1994 | Thygesen | |
| 5,311,875 A | 5/1994 | Stasz | |
| 5,313,937 A | 5/1994 | Zdrojkowski | |
| 5,322,057 A | 6/1994 | Raabe et al. | |
| 5,335,654 A | 8/1994 | Rapoport | |
| 5,335,656 A | 8/1994 | Bowe et al. | |
| 5,343,878 A | 9/1994 | Scarberry et al. | |
| 5,353,788 A | 10/1994 | Miles | |
| 5,373,842 A | 12/1994 | Olsson et al. | |
| 5,388,571 A | 2/1995 | Roberts et al. | |
| 5,398,673 A | 3/1995 | Lambert | |
| 5,400,777 A | 3/1995 | Olsson et al. | |
| 5,404,871 A | 4/1995 | Goodman et al. | |
| 5,433,193 A | 7/1995 | Sanders et al. | |
| 5,443,061 A | 8/1995 | Champain et al. | |
| 5,458,137 A | 10/1995 | Axe et al. | |
| 5,479,920 A | 1/1996 | Piper et al. | |
| 5,490,502 A | 2/1996 | Rapoport et al. | |
| 5,492,113 A | 2/1996 | Estes et al. | |
| 5,503,146 A | 4/1996 | Froehlich et al. | |
| 5,509,404 A | 4/1996 | Lloyd et al. | |
| 5,509,414 A | 4/1996 | Hok | |
| 5,517,983 A | 5/1996 | Deighan et al. | |
| 5,522,382 A | 6/1996 | Sullivan et al. | |
| 5,526,805 A | 6/1996 | Lutz et al. | |
| RE35,295 E | 7/1996 | Estes et al. | |
| 5,535,738 A | 7/1996 | Estes et al. | |
| 5,535,739 A | 7/1996 | Rapoport et al. | |
| 5,537,997 A | 7/1996 | Mechlenburg et al. | |
| 5,540,219 A | 7/1996 | Mechlenburg et al. | |
| 5,540,220 A | 7/1996 | Gropper | |
| 5,546,933 A | 8/1996 | Rapoport et al. | |
| 5,551,418 A | 9/1996 | Estes et al. | |
| 5,551,419 A | 9/1996 | Froehlich et al. | |
| RE35,339 E | 10/1996 | Rapoport | |
| 5,567,127 A | 10/1996 | Wentz | |

| | | | | | | |
|---|---|---|---|---|---|---|
| 5,570,682 | A | 11/1996 | Johnson | GB | 2 254 700 A | 10/1992 |
| 5,598,838 | A | 2/1997 | Servidio et al. | GB | 2 271 811 A | 4/1994 |
| 5,608,647 | A | 3/1997 | Rubsamen et al. | GB | 2 294 400 A | 5/1996 |
| 5,617,846 | A | 4/1997 | Graetz et al. | JP | 54-104369 | 8/1979 |
| 5,632,269 | A | 5/1997 | Zdrojkowski | JP | 60-212607 | 10/1985 |
| 5,633,552 | A | 5/1997 | Lee et al. | JP | 62-103297 | 4/1987 |
| 5,642,730 | A | 7/1997 | Baran | JP | 63-275352 | 11/1988 |
| 5,645,053 | A | 7/1997 | Remmers et al. | JP | 2-173397 | 12/1988 |
| 5,645,054 | A | 7/1997 | Cotner et al. | JP | 4-70516 | 3/1992 |
| 5,655,520 | A | 8/1997 | Howe et al. | JP | 4-70516 | 3/1992 |
| 5,655,522 | A | 8/1997 | Mechlenburg et al. | JP | 6-249742 A | 9/1994 |
| 5,666,946 | A | 9/1997 | Langenback | JP | 06249741 A | 9/1994 |
| 5,682,878 | A | 11/1997 | Ogden | JP | 07280609 A | 10/1995 |
| 5,685,296 | A | 11/1997 | Zdrojkowski et al. | JP | 8019610 | 1/1996 |
| 5,701,883 | A | 12/1997 | Hete et al. | SE | SU 1710064 A1 | 2/1992 |
| 5,704,345 | A | 1/1998 | Berthon-Jones | SE | 467041 B | 5/1992 |
| 5,715,812 | A | 2/1998 | Deighan et al. | WO | WO80/01044 | 5/1980 |
| 5,730,121 | A | 3/1998 | Hawkins et al. | WO | WO 80/01044 | 5/1980 |
| 5,740,795 | A | 4/1998 | Brydon | WO | WO82/03326 | 10/1982 |
| 5,794,615 | A | 8/1998 | Estes | WO | WO82/03548 | 10/1982 |
| 5,823,187 | A | 10/1998 | Estes et al. | WO | WO86/05965 | 10/1986 |
| 6,044,844 | A * | 4/2000 | Kwok et al. ......... 128/207.11 | WO | WO86/06969 | 12/1986 |

FOREIGN PATENT DOCUMENTS

| | | |
|---|---|---|
| AU | A-33877/93 | 4/1993 |
| AU | B-59270/90 | 5/1993 |
| AU | A-38508/93 | 7/1993 |
| AU | A-48748/93 | 9/1993 |
| AU | A-52628/93 | 7/1994 |
| AU | B 79174/94 | 6/1995 |
| AU | A-34471/95 | 2/1996 |
| AU | A-40711/95 | 4/1996 |
| AU | A 39130/95 | 6/1996 |
| AU | B 34354/95 | 5/1998 |
| DE | 459104 | 4/1928 |
| DE | 701 690 | 1/1941 |
| DE | 3015279 A1 | 10/1981 |
| DE | 34 02 603 A1 | 8/1985 |
| DE | 3537507 A1 | 4/1987 |
| DE | 3539073 A1 | 5/1987 |
| DE | 4432219 C1 | 4/1996 |
| EP | 0 062 166 A2 | 10/1982 |
| EP | 0 066 451 A1 | 12/1982 |
| EP | B1 0 088 761 | 9/1983 |
| EP | 0 164 500 A2 | 3/1985 |
| EP | 0 171 321 A1 | 2/1986 |
| EP | 0 185 980 | 7/1986 |
| EP | 0 236 850 A2 | 9/1987 |
| EP | 298 367 A2 | 1/1989 |
| EP | 0 388 525 A1 | 9/1990 |
| EP | 0 425 092 A1 | 5/1991 |
| EP | 0 481 459 A1 | 4/1992 |
| EP | 0549299 A2 | 6/1993 |
| EP | 606 687 A2 | 7/1994 |
| EP | 0705615 A1 | 9/1994 |
| EP | 0 714 670 A2 | 12/1994 |
| EP | 0 656 216 A2 | 6/1995 |
| EP | 0 661 071 A1 | 7/1995 |
| EP | 178 925 A2 | 4/1996 |
| EP | 0 709 107 A1 | 5/1996 |
| EP | 0 788 805 A2 | 8/1997 |
| EP | 0 839 545 A1 | 5/1998 |
| FR | 2 574 657 A1 | 6/1986 |
| FR | 2 672 221 | 8/1992 |
| FR | 2682042 A1 | 4/1993 |
| GB | 1432572 | 4/1976 |
| GB | 1 444 053 | 7/1976 |
| GB | 2 077 444 A | 12/1981 |
| GB | 2147506 | 9/1984 |
| GB | 2 147 506 A | 5/1985 |
| GB | 2 164 569 A | 3/1986 |
| GB | 2 205 167 A | 11/1988 |
| WO | WO88/10108 | 12/1988 |
| WO | WO 90/14121 | 11/1990 |
| WO | WO90/14121 | 11/1990 |
| WO | WO92/11054 | 7/1992 |
| WO | WO92/15353 | 9/1992 |
| WO | WO92/22244 | 12/1992 |
| WO | WO93/08857 | 5/1993 |
| WO | WO 93/08857 | 5/1993 |
| WO | WO93/09834 | 5/1993 |
| WO | WO 93/09834 | 5/1993 |
| WO | WO93/21982 | 11/1993 |
| WO | WO 93/21982 | 11/1993 |
| WO | WO93/24169 | 12/1993 |
| WO | WO94/16759 | 8/1994 |
| WO | WO94/20051 | 9/1994 |
| WO | WO94/23780 | 10/1994 |
| WO | WO95/32016 | 11/1995 |
| WO | WO96/16688 | 6/1996 |
| WO | WO96/40337 | 12/1996 |
| WO | WO97/02064 | 1/1997 |
| WO | WO97/10019 | 3/1997 |
| WO | WO97/10868 | 3/1997 |
| WO | WO97/15343 | 5/1997 |
| WO | WO97/28838 | 8/1997 |
| WO | WO97/41812 | 11/1997 |
| WO | WO98/06449 | 2/1998 |
| WO | WO98/25662 | 6/1998 |
| WO | WO98/33433 | 8/1998 |
| WO | WO98/35715 | 8/1998 |
| WO | WO98/36338 | 8/1998 |
| WO | WO98/47554 | 10/1998 |
| WO | WO98/57691 | 12/1998 |

OTHER PUBLICATIONS

Int'l. Appn. No. PCT/US79/01063 filed Nov. 27, 1979—WO 8001044, May 29, 1980.
Search Report for EP Application No. 92311645.3, filed Dec. 21, 1992.
Mark Kantrowitz, Erik Horskotte and Cliff Joslyn; "Answers to Frequently Asked Questions about Fuzzy Logic and Fuzzy Expert Systems" Version 1.24 last Modified 20 2 96.
Newl Breas PV 100 CPAP First Class Quality and Function. At the right Price; Jul. 4, 1998, pp. 1-2.
PV 101 Bi Level CPAP and PV 102 Bi-Level Time; pp. 1-3.
Prodigy Medical Supplies Co. Ltd.; CPAP.
Puritan Bennett; Companion 318 Nasal CPAP System; May 1993.
Nellcor Puritan Bennett; Announcing the Goodnight 314 and GoodKnight 318 Nasal CPAP Systems.
Puritan Bennett; Clean, Quiet, and Comfortable . . . The Companion's 515 Nasal CPAP System; Jun. 1988.

DeVilbiss Night Guard Nasal CPAP for the Treatment of Obstructive Sleep Apnea.
Sunrise; DeVilbiss Horizon LT 8001 Nasal CPAP Therapy Small in Size, big on features; Aug. 1997.
Devilbiss; Revitalizer Soft Start; The Facts Speak for Themselves, 1992.
Tranquility; Performance CPAP Advantage.
Healthdyne International; Tranquility Plus.
Respironics Inc.; Respironics' Solo CPAP System Provides Simplified OSA Therapy at an Outstanding value; Sep. 19, 1996.
Respironics Inc.; The First Family of OSA Therapy; 1991.
Fisher & Paykel Healthcare; HC200 Series Nasal CPAP Blower & Heated Humidifier.
Pierre Medical; Morphee Plus appareil de traitement des apnees du sommeil manuel d'utilisation.
Weinmann:Hamburg; Somnotron nCPAP-Great WM 2300, Nov. 1991.
Puritan Bennett; 515a Part of Our Blueprint for the Future; Mar. 1990.
Puritan Bennett; Companion 320 I/E Bi-Level Respiratory System; Apr. 1993.
ResMed; Sullivan VPAP II & II ST.
ResMed; The Sullivan V Family of CPAP Systems; 1996.
ResMed; The AutoSet Portable II; 1997.
ResMed; Sullivan Nasal CPAP System.
ResMed; The Sullivan IIID; 1995.
ResMed; The Sullivan Comfort; 1996.
DeVilbiss a Division of Sunrise Medical; Expand your Horizons With The Horizons; 1995.
Healthdyne Technologies; Home Health Care Dealer; The Journal of Home Medical Equipment and Services/Supplier; Nov. and Dec. 1997.
Healthdyne International; Tranquility Quest, The Compact CPAP for Greater patient comfort.
AirStep; Medical Products . . . Stand the Test of Time.
MAP Medical Progress for Physician und Patient; The Gentle Therapy of Sleep-Related Breathing Disorders.
Taema; Ventilation CP 90.
DPAP; Breath, by breath, by breath.
Lifecare; Smallest. Quietest. Smartest.
Lifecare; Quiet CPAP System for Maximum Compliance; 1991.
Lifecare; Software Nasal Mask, Custom Nasal Masks; 1991.
Nidek Medical; Silenzio.
Weinmann; Just to Fell Well, Sensitive Sleep Apnea Therapy with Somnotron 3 and Somno-Mask System.
Respironics Inc.; Aria CPAP System; 1993.
Respironics Inc.; SleepEasy III A New Dawn in Patient Compliance.
Respironics Inc.; Muliple Choice REMstar Choice Nasal CPAP System.
MaxII nCPAP and Moritz II Bi-Level Brochure.

* cited by examiner

PATIENT INTERFACE FOR RESPIRATORY APPARATUS

CROSS REFERENCE TO RELATED APPLICATIONS

This application is a Divisional Application of U.S. application Ser. No. 08/524,148, filed Sep. 6, 1995, now abandoned, which is a Continuation of U.S. application Ser. No. 07/994,153, filed Dec. 21, 1992, now abandoned, the specifications and drawings of which are incorporated herein by reference.

BACKGROUND OF THE INVENTION

The present invention relates to an improved CPAP respiratory apparatus which will increase patient comfort and therefore compliance.

The fundamental disclosure of CPAP is made in the specification of PCT/AU82/00063 published under WO 82/03548 which discloses the supply of air to the nose of the patient at an elevated pressure, the air being supplied through a large bore inlet tube. The elevated pressure at which the air is supplied is approximately 10 cm water gauge although pressures in the range of approximately 5–20 cm water gauge are encountered. However, this pressure is measured while the patient is not breathing and as the patient inspires and expires the pressure in the patient's mask rises and falls typically by approximately 1–2 cm above and below the steady state level. The large bore inlet tube has an unrestricted internal diameter of approximately 20 mm and thus does not introduce unacceptably high pressure drops and swings in the gas delivery system during breathing. All commercially available devices have standardised to this size and arrangement.

For the patient, the work of breathing increases in proportion to the size of the pressure swing during the respiration cycle. In particular, the discomfort experienced by the patient also increases in proportion to the increase in mask pressure during breathing out. In order to deliver the patient's breathing air requirements without significant pressure loss in the supply tube, which would create a relatively large pressure swing during the breathing cycle, the delivery tube and inlet to the nose mask were selected to be substantially unrestricted and to have the large bore of approximately 20 mm.

However, this arrangement and tubing size are not particularly convenient as far as the comfort of the patient and control of the treatment are concerned. In practice, patients wearing nose masks or equivalent devices including such tubing can turn only from side to side and the freedom of movement of the patient is impaired by the tubing. If the tubing and nose mask could be made smaller, and more acute changes in the direction of air flow tolerated, a much more comfortable and acceptable air delivery system would result. Also if a humidifier and/or a filter could be placed between the pump and the mask, then patient comfort could be increased. Similarly, if a flow measuring device could be so located, control of treatment could be enhanced.

It is the object of the present invention to substantially overcome or ameliorate the above mentioned difficulties by the provision of a CPAP respiratory apparatus which maintains the pressure of air or other breathable gas at the point of immediate access to the patient's respiratory system substantially constant notwithstanding in-line components which introduce appreciable pressure drops.

It is appreciated that increasing the resistance to flow in the supply tube results in an increased pressure drop between the "pump end" and "patient end" of the delivery tube. In order to compensate for this pressure drop between the ends of the delivery tube whilst maintaining flow, the present invention seeks to maintain the air pressure at the "patient end" substantially constant. This is done by sensing the pressure within the nose mask, or equivalent device, itself.

Two known commercially available CPAP respiratory devices involve some pressure or air flow control. One of these is the device sold by RESPIRONICS of the USA under the trade name BiPAP in which the supply pressure can be switched between a lower pressure and a higher pressure in accordance with the patient's respiratory cycle in order to assist the patient's breathing effort. This switching is achieved by sensing air flow through a sensor in the pump of the air supply system. Another commercially available device sold by HEALTHDYNE also of the USA has a control mechanism which controls the pressure at the outlet of the air pump.

Both of these commercially available devices use the standard large bore 20 mm inlet tubing which is substantially unrestricted downstream of the pump outlet and will not operate satisfactorily with pressure drop inducing components such as small bore tubing. This is thought (as will be apparent from the experimental data given hereafter) to be due to the large pressure drop which causes large pressure swings in the nose mask as the patient inspires and expires. In particular, because these prior art devices do not attempt to derive the signal to control the operation at the air pump as near to the patient's respiratory system as possible, and downstream of all pressure drop inducing components, there is a problem of time lags and phase shifts as regards the supply of air to and from the patient. It has been experimentally determined by the applicant that by sensing the pressure at the patient's mask and servo-controlling same to be substantially constant, the problems introduced by the pressure drop created in the supply tubing, can be substantially overcome.

SUMMARY OF THE INVENTION

In accordance with the first aspect of the present invention there is disclosed a CPAP respiratory apparatus comprising a breathable gas delivery device adapted to deliver breathable gas to the inlet of a patient's respiratory system, a breathable gas supply means having an outlet and arranged to supply breathable gas to said outlet at a pressure above atmospheric pressure, and a flexible conduit having an internal bore and being connected between said outlet and said gas delivery device wherein a pressure transducer is connected to said device to sense the pressure at said respiratory system inlet, and a servo-controller is connected to both said gas supply means and said pressure transducer to adjust the operation of said gas supply means to maintain the pressure at said respiratory system inlet substantially constant.

Preferably, at least that portion of said conduit closest to said nose mask has an internal bore which is relatively small compared with the remainder of the conduit.

In accordance with a second aspect of the present invention there is disclosed a method of operating a breathable gas supply means of a CPAP respiratory apparatus comprising a breathable gas delivery device adapted to deliver breathable gas to the inlet of a patient's respiratory system and connected by a flexible conduit to an outlet of said gas supply means to receive breathable gas therefrom at a pressure above atmospheric pressure, said method comprising the steps of sensing the pressure supplied to said respiratory system inlet by said gas delivery device, and using the sensed pressure to servo-control said gas supply means to maintain the pressure at said respiratory system inlet substantially constant.

Preferably, at least one pressure drop inducing device is located in the gas supply line between the pump and patient.

BRIEF DISCUSSION OF THE DRAWINGS

Some embodiments of the present invention will now be described with reference to the drawings in which.

DETAILED DESCRIPTION OF THE PREFERRED EMBODIMENTS

Figures 1, 2, 3, 4:
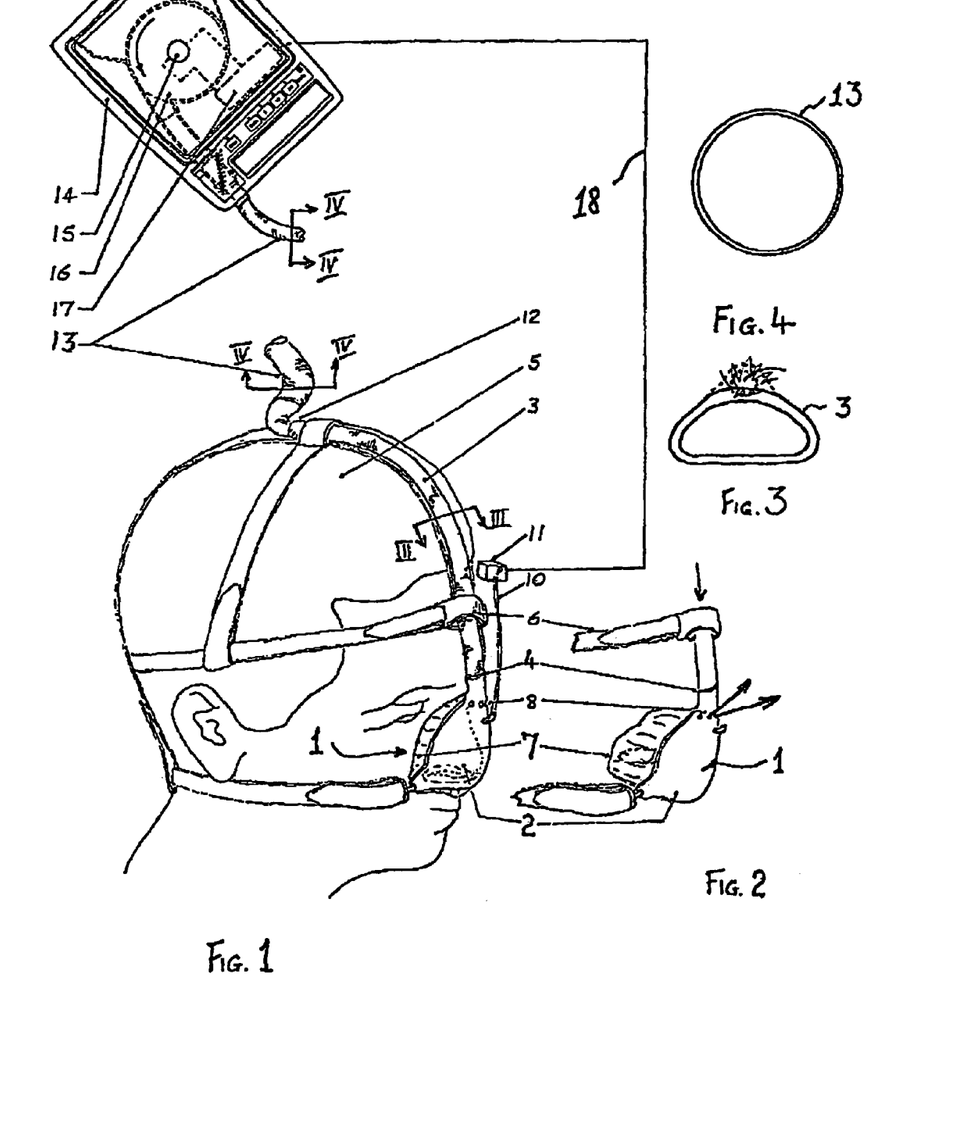
FIG. 1 is a schematic perspective view of the nose mask and air supply tube of the CPAP respiratory apparatus of a first embodiment.
FIG. 2 is a partial perspective view of the mask only with its membrane distended.
FIGS. 3 and 4 are cross-sectional views along the lines III—III and IV—IV of FIG. 1 respectively.

As seen in FIG. 1 a nose mask 1 is of generally known configuration and is substantially as disclosed in Australian Patent Application No. 77110/91. The mask 1 takes the form of a shell 2 of firm plastics which is shaped to fit over at least the nose region of the patient. A distendable membrane 7 is mounted on the shell 2 and forms a face contacting portion for the mask 1. The shell 2 and membrane 7 together define a chamber which receives the patient's nose. The chamber communicates with an air or other breathable gas supply aperture to which a short length of supply tube 3 is connected. The aperture is preferably provided with at swivel joint 4 so that the supply tube 3 can rotate relative to the remainder of the face mask 1. This prevents the supply tube 3 from becoming inadvertently twisted. The nose mask 1 is retained on the patient 5 by means of conventional straps 6.

In the vicinity of the swivel joint 4 are located a series of apertures 8 through which air or other breathable gas exits to atmosphere as indicated by the arrows in the drawing. Pressure is sensed in the interior chamber of mask 1 by a thin flexible pipe 10 which is connected a pressure transducer 11 which provides a continuously sensed electrical output signal carried on cable 18 to a servo-controller 17 for the pump 14.

The supply tube 3 is of a small bore (typically having an effective internal diameter of 9–15 mm) and thus the patient whilst sleeping cannot roll onto an uncomfortable large bore tube. As indicated in FIG. 3 the small bore supply tube 3 in this embodiment has a substantially triangular cross-sectional shape and is flexible. The term "effective internal diameter" means the diameter of a tube of circular internal cross-sectional shape which has the same internal cross-sectional area.

Preferably a swivel joint 12 connects the small bore supply tube 3 to a substantially conventional large bore supply tube 13. The pipe 10 which typically has a very small bore, or the cable 18 can conveniently be connected alongside the supply tubes 3, 13. This supports the pipe 10 yet enables the pressure transducer 11 to be located either at, or remote from, the nose mask 1. If desired, the pipe 10 and tube 3 can be combined in a single moulding. Alternatively, if the pressure transducer 11 is located within, or adjacent to, the mask the electrical outputs signal cable 18 of the transducer can be conveyed to the servo-controller 17 via small pipe 10.

The large bore supply tube 13 is connected to a pump 14 which consists essentially of an electric motor 15 and fan 16. The pump 14 preferably supplies air, however, other breathable gases such as mixtures of air and oxygen can be supplied in known fashion. The term "air" shall be used hereafter for such gases. The electric motor 15 is controlled by a substantially conventional servo-controller 17 which receives as an input, the output from the pressure transducer 11. If desired, the pipe 10 can be sufficiently long to locate the transducer 11 at the pump 14.

It will be apparent to those skilled in the art that the pressure transducer 11 and servo-controller 17 enable the operation of the electric motor 15 to be controlled so as to maintain the air pressure within the nose mask 1 substantially constant throughout the respiration cycle. As a result, the electric motor 15 accommodates in its operation the fluctuating internal pressure drop created by both the patient's breathing and the small bore of the supply tube 3. In particular, the supply conduit interconnecting the mask 1 and air pump 14 can now have a small bore (in the range of from 9 to 15 mm in internal diameter) over at least part of its length. Particularly over that section in the region of the patient's face and head. This represents a decrease in available cross-sectional area of the supply tube 3 from 43.75% to 79.75% respectively.

Because the supply tube 3 has such a reduced bore, the tube is much more flexible and comfortable for the user and can conveniently be fixed to the straps 6 used for holding the nose mask on the patient's face. In particular, it is not generally possible to lie upon the 20 mm large bore tubing without feeling discomfort, however, with the relatively small bore supply tube 3 this is possible. As a consequence, the patient's comfort is substantially increased. This increases the patient's compliance, especially after the more pronounced symptoms of sleep apnea have been initially ameliorated. The increased compliance is of particular importance in the long term treatment of the patient.

Comparative Tests

The above described apparatus was tested alongside the above mentioned commercially available BiPAP (Respironics) device and TRANQUILITY PLUS device (the trade name of the Healthdyne product).

For the experiment, the large bore supply tube 13 took the form of standard 20 mm bore tubing. The length of the small bore supply tube 3 was 17 cm. All three units were tested with the same breathing simulator which delivered a substantially sinusoidal air flow having a 500 ml tidal volume at 12 cycles/minute. The peak flow during both inspiration and expiration was 50–60 litres per minute.

For each air pump arrangement (BiPAP, TRANQUILITY PLUS and air pump 14) three types of masks were used. The first was a conventional mask with a 20 mm constant diameter supply tube (in the case of BiPAP and TRANQUILITY PLUS the mask and tube were as supplied with the equipment). The second mask was the mask 1 with the supply tube 3 being of circular cross-section and of 15 mm internal diameter. The third mask was the mask 1 but with 9 mm internal diameter for the supply tube 3.

The results for 5 different levels of CPAP pressure (0, 5, 10, 15 and either 17 or 20 cm water gauge) are set out in Table 1. The figures given are air pressures in cm of water gauge with $P_{stat}$ being the average or static pressure within the mask whilst $\Delta P_{tot}$ is the combined pressure swing during the inspiration/expiration cycle of the breathing simulator.

It can be seen that the combined pressure swing $\Delta P_{tot}$ increases significantly with decreasing tubing diameter with the HEALTHDYNE and BiPAP units, while the servo-controlled unit 14 maintains pressure in the mask 1 generally to better than 1 cm total swing for all sizes of tubing. It follows therefore that an improved result allowing the use of the more comfortable small bore tubing, has been achieved.

Figure 5:
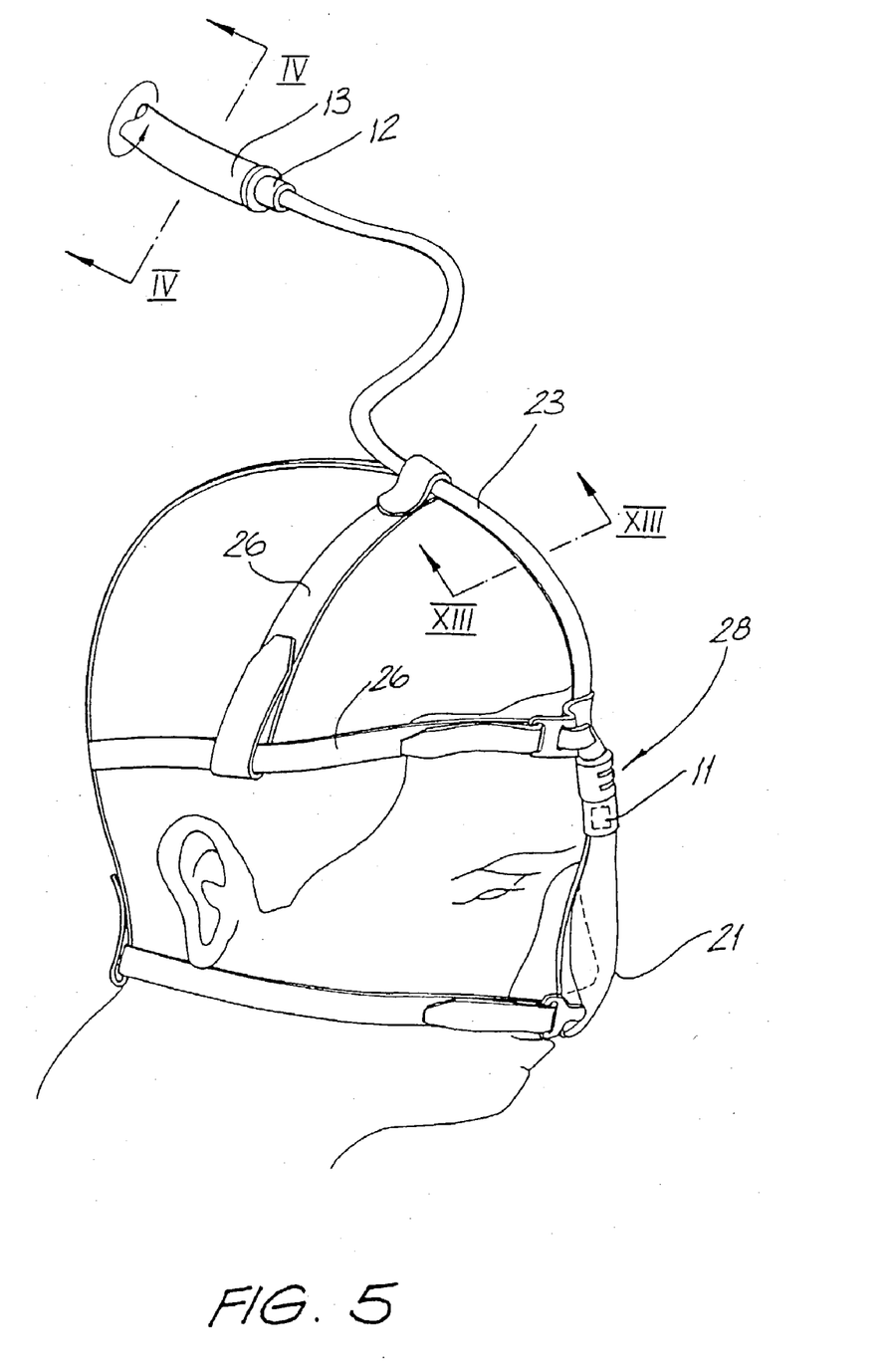
FIG. 5 is a perspective view of the nose mask, harness and supply conduit of a second embodiment.
Figures 10, 11, 12, 13:
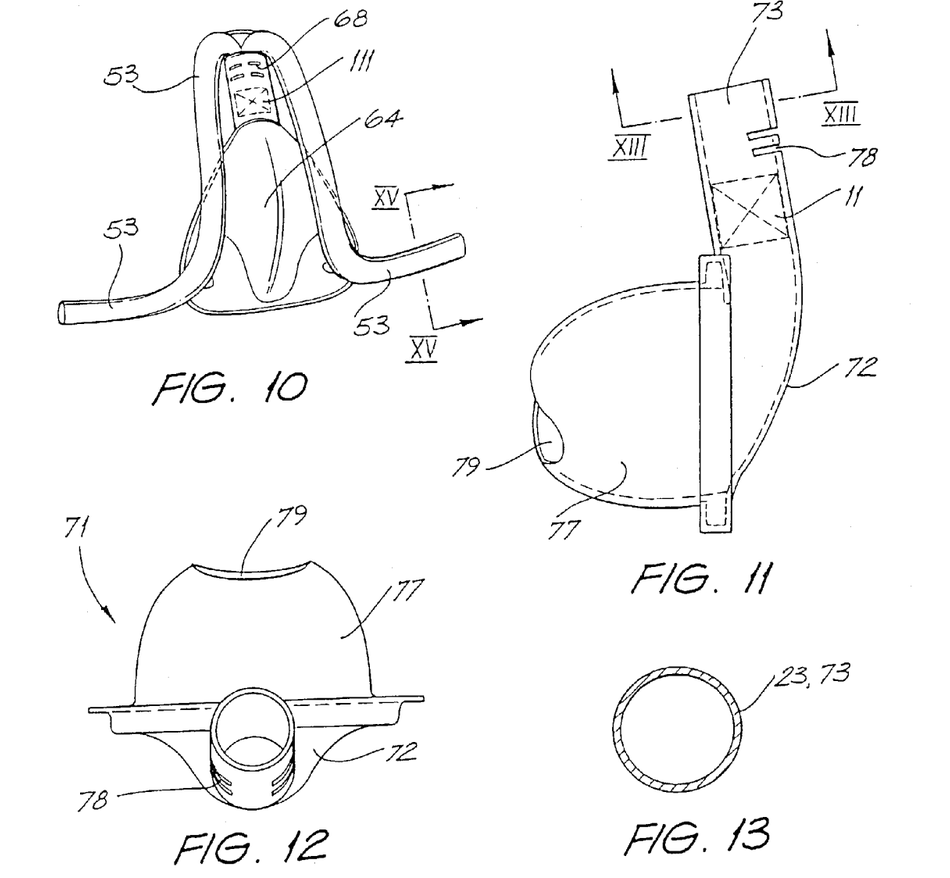
FIG. 10 Is a front view of the nose mask of FIG. 8.
FIG. 11 is a side elevation of an alternative nose mask.
FIG. 12 is a plan view of the nose mask of FIG. 11.
FIG. 13 is a cross-sectional view taken along the line XIII—XIII of FIGS. 5, 6 and 11.

A second embodiment is illustrated in FIG. 5 where like parts are indicated by a designator increased in magnitude by 20. Thus, the mask 21 of the second embodiment is a face mask and includes a pressure transducer 11 located within the mask 21 as indicated by broken lines in FIG. 5. The transducer 11 Is located within the mask 21 and between the patient's nose and the apertures 8. A substantially similar arrangement of straps 26 retains the nose mask 21 in position. As indicated in FIG. 13, the cross-sectional shape of the small bore inlet tube 23 is circular. Again, the small bore inlet tube 23 is connected to the conventional large bore inlet tube 13 by means of a substantially conventional swivel joint 12.

Figure 6:
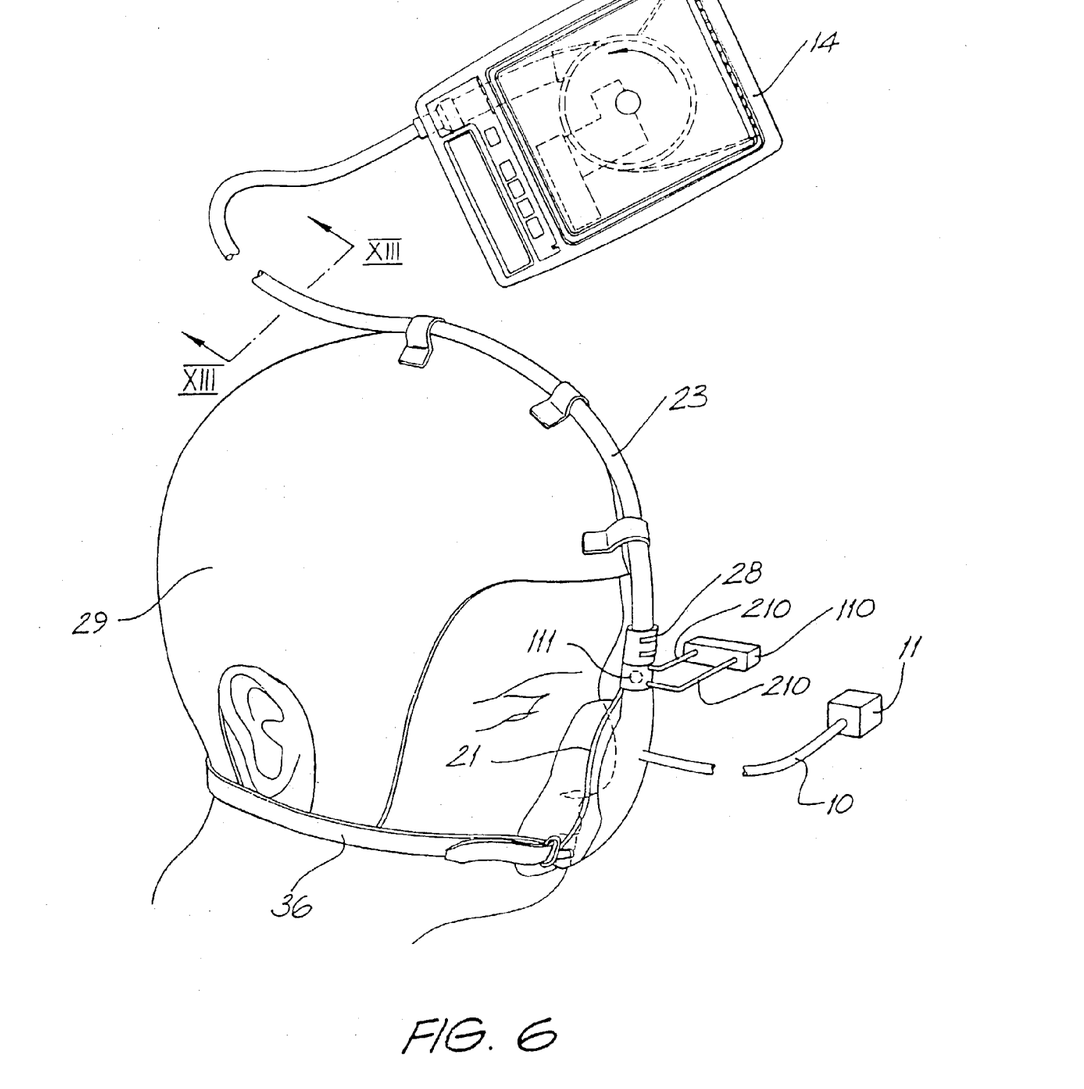
FIG. 6 is a view similar to FIG. 5, but of a third embodiment.

A third embodiment is illustrated in FIG. 6 in which the nose mask 21 and small bore inlet tube 23 are substantially as in FIG. 5. However, a flow orifice 111 (preferably of the type disclosed in U.S. Pat. No. 4,006,635 [Billette]) only is located in the mask 21 and is connected by two small tubes 210 to a flow transducer 110. The tubes 210 are located one upstream and one downstream of the flow orifice 111. As before, the pressure transducer 11 is connected to the mask 21 via the tube 10. In addition, a cap 29 with straps 36 is provided for the patient in order to secure the small bore inlet tube 23.

Figure 7:
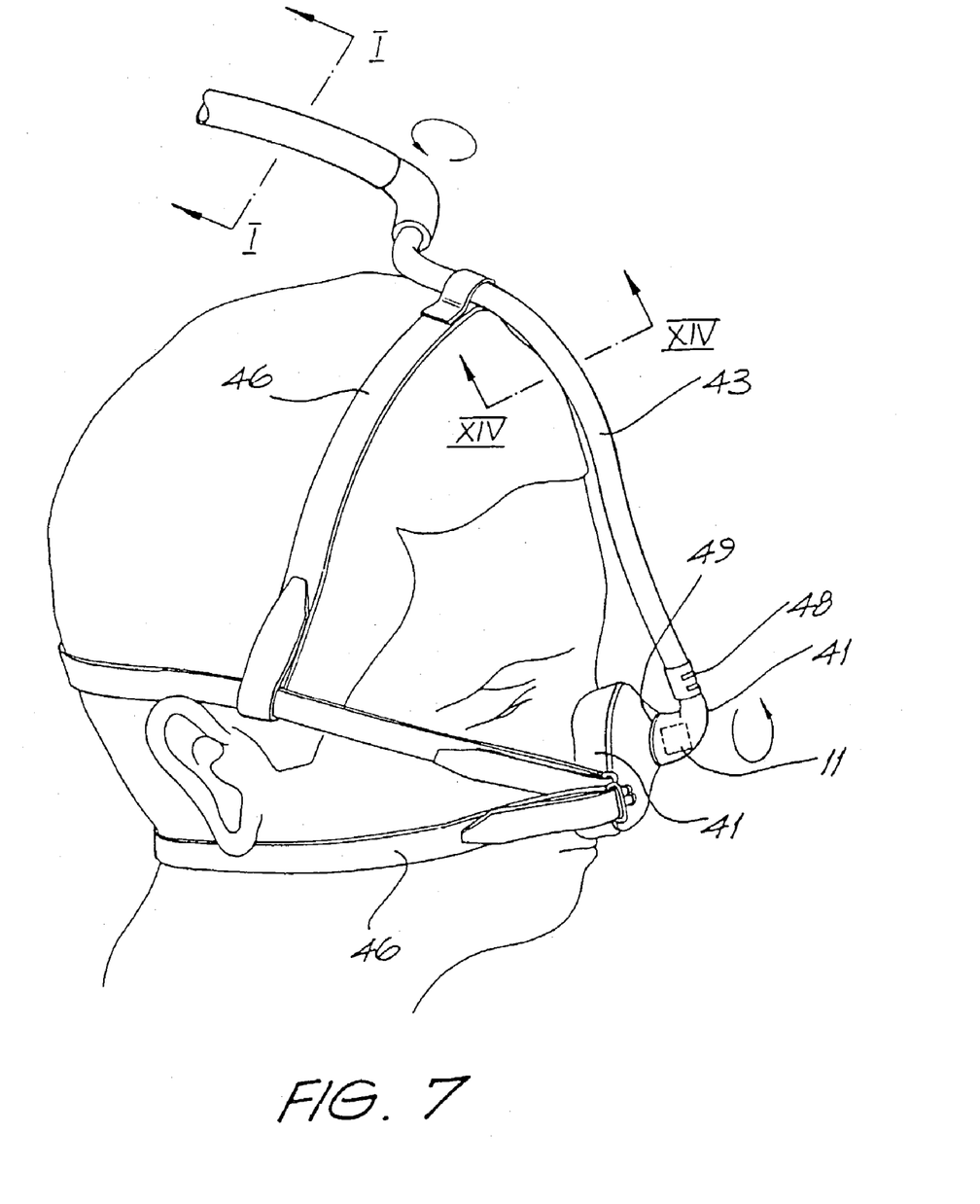
FIG. 7 is a view similar to FIG. 5, but of a fourth embodiment.

A fourth embodiment is illustrated in FIG. 7 in which like parts have their designator increased in magnitude by 40 relevant to the embodiment of FIG. 1. It will be seen that the configuration of the nose mask 41 is changed so as to provide a swivel joint 49 which is sufficiently large to accommodate the pressure transducer 11 which is again located downstream of the apertures 48. The configuration of the straps 46 is also different and provides an alternative securing arrangement.

Figure 8:
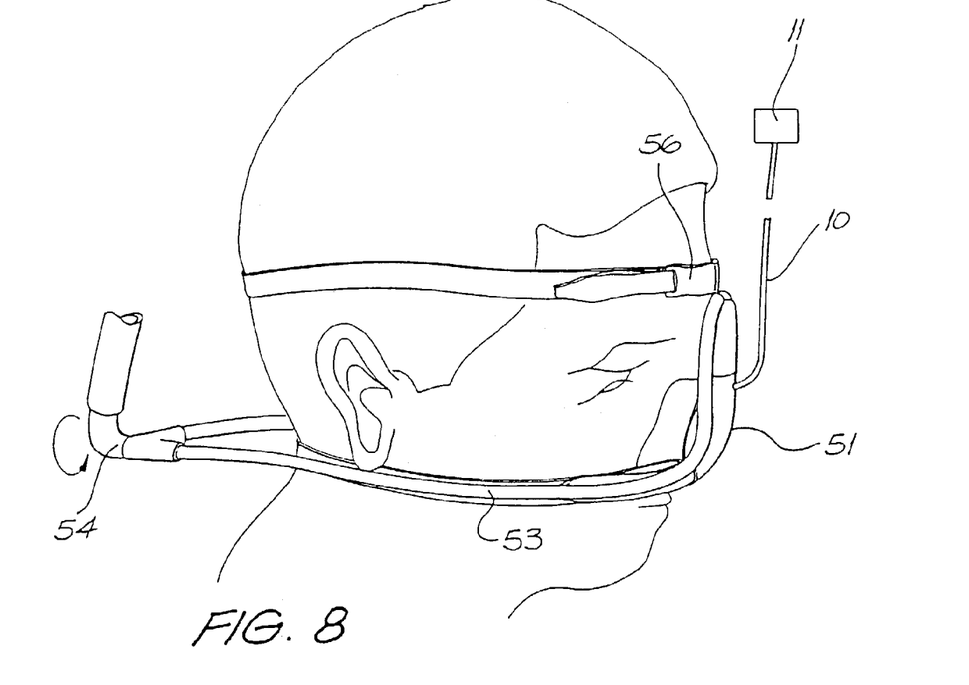
FIG. 8 is a view similar to FIG. 5, but of a fifth embodiment.
Figure 9:
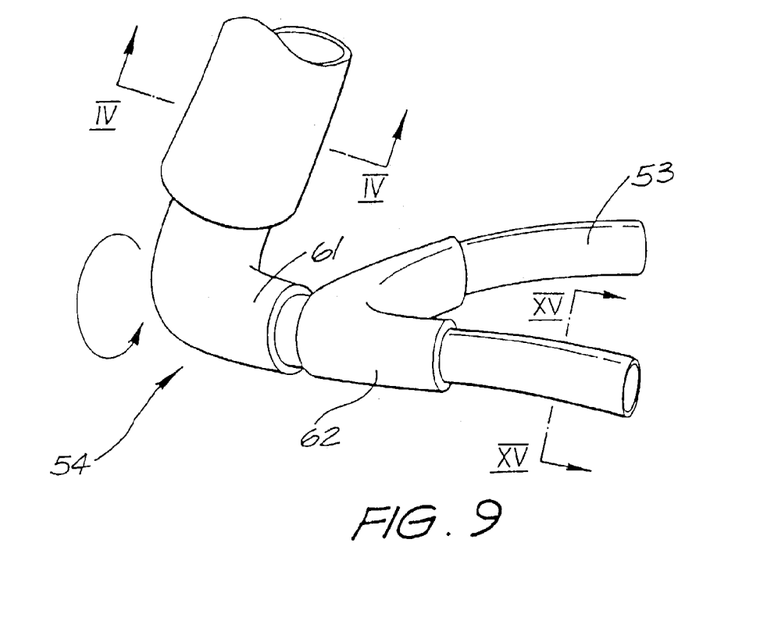
FIG. 9 is an enlarged view of the branched connector of FIG. 8.

FIGS. 8–10 illustrate a fifth embodiment in which a nose mask 51 is supplied by means of a split or dual inlet tubes 53 each of which is supplied from a branch swivel connector 54 illustrated in more detail in FIG. 9. The connector 54 is located to the rear of the patient's head and the nose mask 51 is secured in position by means of a forehead strap 56.

As seen in FIG. 9, the branch connector 54 includes an elbow 61 which swivels as indicated by the arrow in FIG. 95 relative to a Y-piece 62. The inlet tubes 53 are sealed directly to the Y-piece 62.

Figure 15:
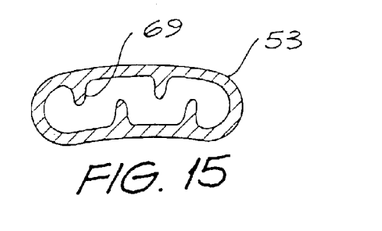
FIG. 15 is a cross-sectional view taken along the line XV—XV of FIGS. 9 and 10.

FIG. 10 illustrates further detail of the nose mask 51 and, in particular, illustrates the cavity 64 which receives the patient's nose. The flow orifice 111 is located within the inlet to the cavity 64 as are the exit apertures 68. It will be seen that the inlet tubes 53 extend across each cheek of the patient and alongside the nose mask 51. As seen in FIG. 15, the inlet tubes 53 preferably have a flat configuration and are provided with a plurality of internal ribs 69 which prevent the inlet tube 53 being crushed between the pillow and the patient's head.

Turning now to FIGS. 11 and 12, a still further embodiment of the nose mask 71 is illustrated. The nose mask 71 has a substantially rigid outer shell 72 which has an inlet 73 of substantially circular cross-section which includes exit apertures 78 and is sufficiently large to accommodate the pressure transducer 11 as illustrated (or the flow transducer 110-not illustrated). Sealingly connected to the outer shell 72 is a soft membrane 77 which is shown in FIGS. 11 and 12 in its distended position and has a nose receiving aperture 79. Once the nose of the patient is inserted into the aperture 79, the membrane 77 then conforms itself to the surface of the patient's skin thereby providing an effective seal.

Figure 14:
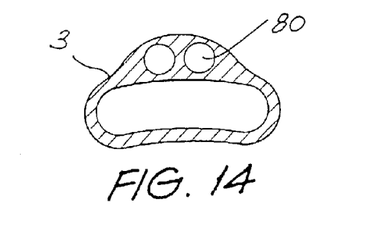
FIG. 14 is a cross-sectional view taken along the line XIV—XIV of FIG. 7.

As indicated in FIG. 14, if desired the inlet tube 35 and equivalents, can be provided with two internal passageways 80 which can be used either to transmit pressure from the region adjacent the patient's nose or to locate the electric cable(s) from transducers.

With the above described distendable mask, the deformable membrane has hitherto stretched and compressed with changes in the mask pressure. This oscillation is somewhat disturbing to the patient and is substantially eliminated in accordance with the above since the servo-controller 17 maintains the mask pressure substantially constant throughout the respiration cycle.

Furthermore, most of the noise escaping from a CPAP device comes either from the air inlet or air outlet. This can be reduced by placing baffles in the air inlet and/or the air outlet, but with the prior art devices this is at the expense of increasing the pressure drop and pressure swings in the mask during inspiration and expiration.

In accordance with the above described arrangements, this additional baffling can be added and the pressure swings that would otherwise result can be compensated for by servo-controlling the pressure in the mask. Since mask comfort and noise level are the two most important determinants of patient comfort and compliance, this represents a substantial advantage.

Figure 16:
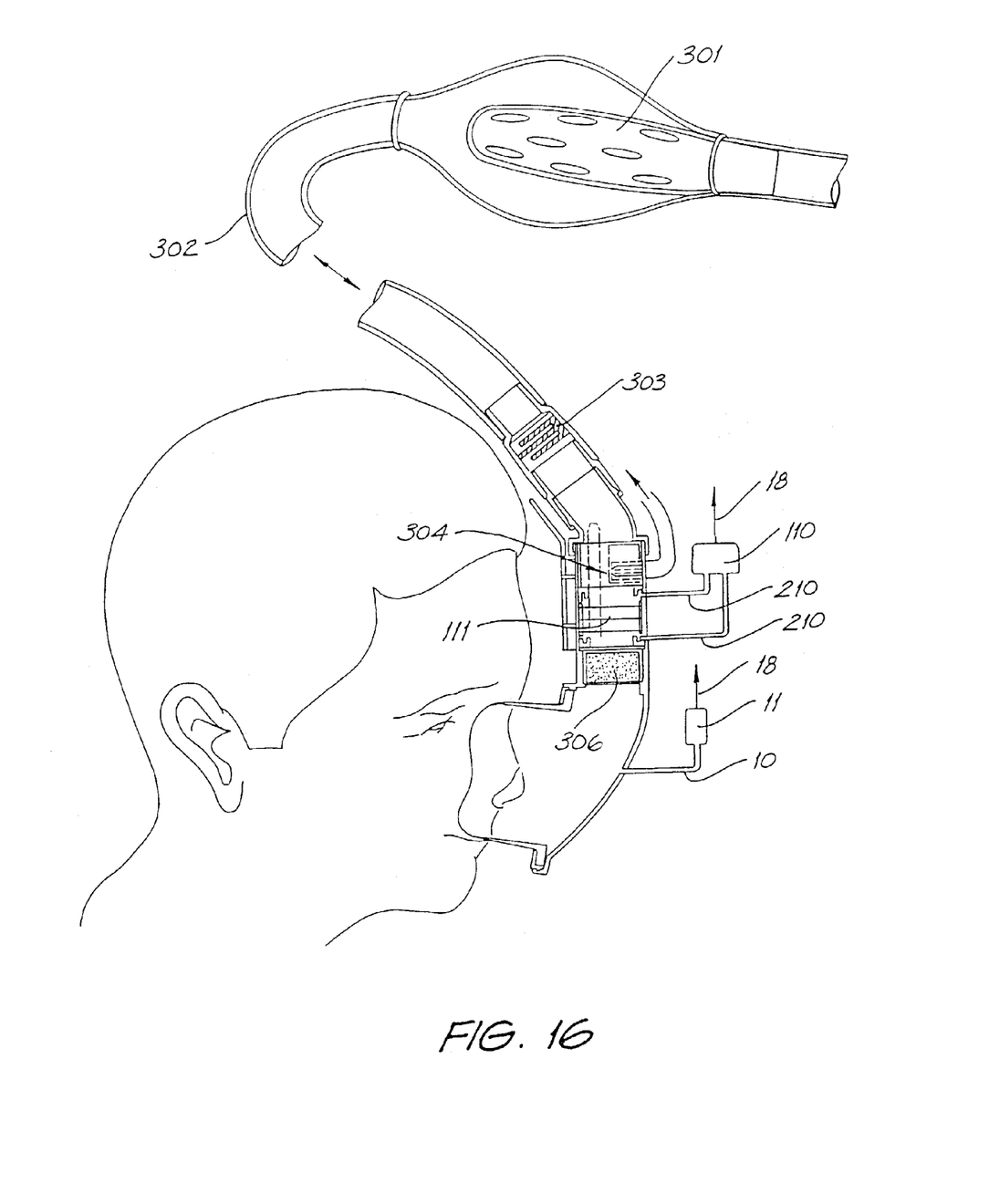
FIG. 16 is a view similar to FIG. 1 but illustrating a further embodiment having various different types of pressure drop inducing components.

Like the small bore tube 3, 23 and the connector 54, such baffles represent pressure drop inducing components. As indicated in FIG. 16, such components can take the form of baffles 301, sharp bends 302, a filter 303, a high pressure drop air outlet diffuser 304 having a diverting tube to direct flow away from a sleeping partner, a flow orifice 111 and a humidifier 306 such as a hydroscopic condensing humidifier made by ICOR AB of Sweden. The pressure drop introduced by any or all of these "accessories" can be accommodated so as to maintain the pressure at the patient's nose substantially constant.

If desired, the transducers 11,110 can be located at or near the mask as illustrated and connected by cables 18 to the control apparatus 17. Alternatively, the tubes 10,210 can be sufficiently long to enable the transducers 11, 110 to be located adjacent the pump 14. This arrangement has the advantage that no electric cables are located near the patient.

In addition, if the positions of the flow orifice 111 and humidifier 306 shown in FIG. 16 are reversed, then a combined sensing arrangement is possible. In this arrangement the flow orifice 111 is connected to the flow transducer 110 as before via two tubes 210. The downstream one of the tubes 210 is branched to provide the tube 10 for the pressure transducer 11.

The foregoing describes only some embodiments of the present invention and modifications, obvious to those skilled in the art can be made thereto without departing from the scope of the present invention.

For example, although a nose mask is described and illustrated in detail, a full face mask or nasal prongs (not shown) can also be used.

TABLE I

|  | Pstat | ΔPtot | Pstat | ΔPtot | Pstat | ΔPtot | Pstat | ΔPtot | Pstat | ΔPtot |
|---|---|---|---|---|---|---|---|---|---|---|
| BIPAP UNIT | | | | | | | | | | |
| Conv. Mask |  |  | 0.5 | 1.00 | 10.0 | 1.20 | 15.0 | 1.40 | 20.00 | 2.40 |
| New Mask 15 |  |  |  | 1.20 |  | 1.30 |  | 1.40 |  | 2.00 |
| New Mask 9 |  |  |  | 2.20 |  | 2.70 |  | 3.80 |  | 5.40 |
| HEALTHDYNE TRANQUILITY PLUS | | | | | | | | | | |
| Conv. Mask | 0.0 | 0.70 | 5.0 | 0.85 | 10.0 | 1.10 | 15.0 | 1.35 | 17.00 | 1.40 |
| New Mask 15 |  | 1.20 |  | 1.40 |  | 1.80 |  | 2.10 |  | 2.20 |
| New Mask 9 |  | 2.20 |  | 3.20 |  | 4.20 |  | 4.80 |  | 5.10 |
| SERVO-CONTROLLED UNIT 14 | | | | | | | | | | |
| Conv. Mask | 0.0 | 0.40 | 5.0 | 0.35 | 10.0 | 0.45 | 15.0 | 0.60 | 20.00 | 0.90 |
| New Mask 15 |  | 0.75 |  | 0.48 |  | 0.52 |  | 0.65 |  | 0.95 |
| New Mask 9 |  | 0.90 |  | 1.05 |  | 0.65 |  | 0.75 |  | 0.90 |

The invention claimed is:

1. A patient interface assembly adapted to be connected to a gas supply pump to deliver breathable gas to the inlet of a patient's respiratory system comprising:

a supply conduit;

a patient interface;

a branch swivel connector including a Y-piece and an elbow that swivels relative to the Y-piece, the branch swivel connector being adapted to be located to the rear of a patient's head in use and being connected to the supply conduit;

a pair of inlet tubes each having a first end positioned in use near a mouth of a patient and being connected to the patient interface, a middle portion arranged to pass across a cheek of a patient and an end portion being joined to the Y-piece of the branch connector, the inlet tubes having a cross-sectional configuration including a substantially flat exterior surface and an interior surface provided with a plurality of internal ribs to prevent the tubes being crushed; and a strap secured to the patient interface and adapted to pass around the sides and rear of the head to hold the patient interface in position on the head, wherein each inlet tube includes generally parallel, opposing upper and lower side walls, at least a pair of internal ribs extending from one of the upper and lower side walls, and at least one internal rib extending from the other of the upper and lower side walls, and wherein the at least a pair of internal ribs extending from one of the upper and lower side walls are offset from the at least one internal rib extending from the other of the upper and lower side walls to substantially prevent engagement between the internal ribs upon compression of the upper and lower side walls.

2. The patient interface assembly as claimed in claim 1, wherein the patient interface includes a nose mask.

3. The patient interface assembly as claimed in claim 1, wherein the patient interface includes a full face mask.

4. The patient interface assembly as claimed in claim 1, wherein the patient interface includes nasal prongs.

5. A patient interface assembly adapted to be connected to a gas supply pump to deliver breathable gas to the inlet of a patient's respiratory system comprising:

a supply conduit;

a patient interface;

a connector having an end portion connected to the supply conduit;

at least one inlet tube connected between the patient interface and an opposite end portion of the connector, the tube having a substantially flat configuration that provides a substantially flat exterior surface and a plurality of internal ribs that extend inwardly from an interior surface thereof which prevent the tube from being crushed; and at least one strap structured to hold the patient interface in position on the patient's head, wherein each inlet tube includes generally parallel, opposing upper and lower side walls, a pair of upper internal ribs extending from the upper side wall, and a pair of lower internal ribs extending from the lower side wall, and wherein the pair of upper internal ribs are offset from the pair of lower internal ribs.

6. The patient interface assembly as claimed in claim 5, wherein the connector is a branch swivel connector including a Y-piece and an elbow that swivels relative to the Y-piece.

7. The patient interface assembly as claimed in claim 5, wherein the patient interface includes a nose mask.

8. The patient interface assembly as claimed in claim 5, wherein the supply conduit provides a bore that is substantially larger than a bore of the inlet tube.

9. A tube for use between a patient interface and a supply of breathable gas, the tube comprising:

a first end portion adapted to be communicated to the patient interface;

a second end portion adapted to be communicated to the supply of breathable gas; and an intermediate portion between the first and second end portions, at least a portion of the intermediate portion having a substantially flat configuration that provides a substantially flat exterior surface and a plurality of internal ribs that extend inwardly from an interior surface thereof which prevent the tube from being crushed, wherein the portion of the intermediate portion includes generally parallel, opposing upper and lower side walls, at least a pair of internal ribs extending from one of the upper and lower side walls, and at least one internal rib extending from the other of the upper and lower side walls, and wherein the at least a pair of internal ribs extending from one of the upper and lower side walls are offset from the at least one internal rib extending from the other of the upper and lower side walls such that, upon compression of the upper and lower side walls, adjacent internal ribs are adapted to define a passageway therebetween.

10. The patient interface assembly as claimed in claim 1, wherein, upon compression of the upper and lower side walls, each internal rib includes a distal end portion adapted to engage the opposing side wall to substantially prevent the interior surfaces of the opposing upper and lower side walls from contacting one another.

11. The patient interface assembly as claimed in claim 1, wherein, upon compression of the upper and lower side walls, adjacent internal ribs are adapted to define a passageway therebetween.

12. The patient interface assembly as claimed in claim 1, wherein the upper side wall provides a pair of upper internal ribs and the lower side wall provides a pair of lower internal ribs offset from the pair of upper internal ribs.

13. The patient interface assembly as claimed in claim 12, wherein, upon substantially full and even compression of the upper and lower side walls, the upper and lower internal ribs define five passageways through the inlet tube.

14. The patient interface assembly as claimed in claim 5, wherein, upon compression of the upper and lower side walls, each upper internal rib includes a distal end portion adapted to engage the opposing lower side wall and each lower internal rib includes a distal end portion adapted to engage the opposing upper side wall to substantially prevent the interior surfaces of the opposing upper and lower side walls from contacting one another.

15. The patient interface assembly as claimed in claim 5, wherein, upon compression of the upper and lower side walls, adjacent upper and lower internal ribs are adapted to define a passageway therebetween.

16. The patient interface assembly as claimed in claim 5, wherein, upon substantially full and even compression of the upper and lower side walls, the upper and lower internal ribs define five passageways through the inlet tube.

17. The tube as claimed in claim 9, wherein, upon compression of the upper and lower side walls, each internal rib includes a distal end portion adapted to engage the opposing side wall to substantially prevent the interior surfaces of the opposing upper and lower side walls from contacting one another.

18. The tube as claimed in claim 9, wherein the upper side wall provides a pair of upper internal ribs and the lower side wall provides a pair of lower internal ribs offset from the pair of upper internal ribs.

19. The tube as claimed in claim 18, wherein, upon substantially full and even compression of the upper and lower side walls, the upper and lower internal ribs define five passageways through the inlet tube.

* * * * *